United States Patent [19]
Ascher et al.

[11] 4,057,557
[45] Nov. 8, 1977

[54] CERTAIN 5-NITROTHIAZOLYLIMIDAZOLIDINE COMPOUNDS

[75] Inventors: Gerd Ascher; Hellmuth Reinshagen, both of Vienna, Austria

[73] Assignee: Sandoz Ltd., Basel, Switzerland

[21] Appl. No.: 655,721

[22] Filed: Feb. 6, 1976

[30] Foreign Application Priority Data

Feb. 13, 1975 Switzerland .................. 1776/75
Feb. 13, 1975 Switzerland .................. 1780/75

[51] Int. Cl.$^2$ ........................................... C07D 417/04
[52] U.S. Cl. ............................ 260/306.8 R; 424/270
[58] Field of Search .................. 260/306.8 R; 424/270

[56] References Cited

U.S. PATENT DOCUMENTS 3,627,777  12/1971  Schmidt et al. ............... 260/306.8 R

*Primary Examiner*—R. Gallagher
*Attorney, Agent, or Firm*—Gerald D. Sharkin; Robert S. Honor; Thomas O. McGovern

[57] ABSTRACT

The invention provides novel 5-nitrothiazolylimidazoline derivatives, useful as chemotherapeutic agents.

12 Claims, No Drawings

CERTAIN 5-NITROTHIAZOLYLIMIDAZOLIDINE COMPOUNDS

This invention provides 5-nitrothiazolylimidazolidine derivatives of formula I,

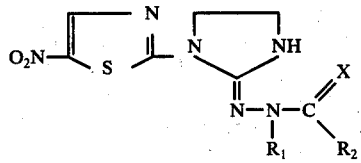

in which
R₁ is hydrogen, lower alkyl or phenyl,
R₂ is hydrogen, lower alkyl or alkoxy, trifluoromethyl, the group —CH=CH—COOH or a group —N(R₃) (R₄), in which R₃ and R₄, which may be the same or different, each signifies hydrogen or lower alkyl, and
X is oxygen, sulphur or imino, provided that when R₂ is lower alkyl or —CH=CH—COOH, then X is oxygen.

As will be appreciated, the compounds of formula I may exist in tautomeric forms of formula Id,

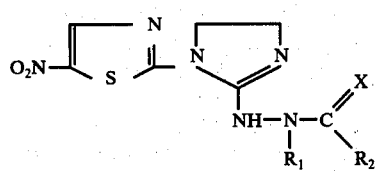

in which R₁, R₂ and X are as defined above.
While reference is hereinafter made only to the form of formula I or the corresponding chemical name, it is to be understood that the invention is not intended to be limited to any particular form of the compounds.

The invention also provides processes for the production of compounds of formula I, comprising a) producing a compound of formula Ia,

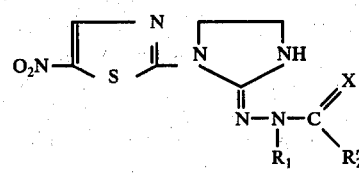

in which
R₁ and X are as defined above, and
R₂' is hydrogen, lower alkoxy, trifluoromethyl, or the group —N(R₃) (R₄), in which R₃ and R₄ are as defined above,
by cyclising a compound of formula II,

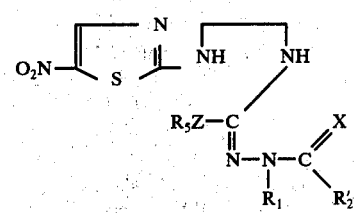

in which

R₁, R₂' and X are as defined above,
R₅ is lower alkyl, and
Z is oxygen or sulphur, b. producing a compound of formula Ib,

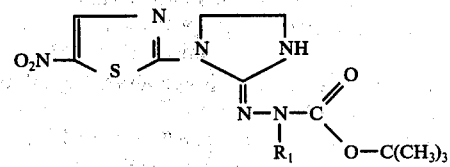

in which R₁ is as defined above,
by reacting a compound of formula III,

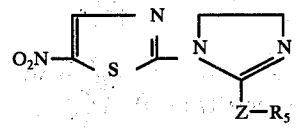

in which R₄ and Z are as defined above,
with the free base form of a compound of formula IVa,

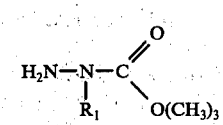

in which R₁ is as defined above,
or
c. producing a compound of formula Ic,

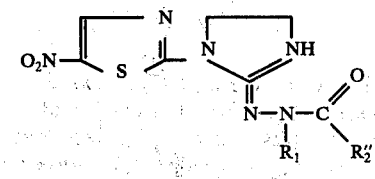

in which
R₁ is as defined above, and
R₂'' is hydrogen, lower alkyl, lower alkoxy other than t-butoxy, trifluoromethyl, the group —CH=CH—COOH, or a group —N(R₃') (R₄'), in which R₃' and R₄', which may be the same or different each signifies lower alkyl,
by acylating a compound of formula Ib with an appropriate acylating agent, while simultaneously splitting off the t-butyloxycarbonyl group in the compound of formula Ib.

The term "lower", as used herein, with reference to alkyl and alkoxy groups means containing, for example 1 to 4, preferably 1 or 2, particularly 1, carbon atom.

The cyclisation in process (a) may be effected in conventional manner, for example at an elevated temperature, preferably at the reflux temperature of the reaction mixture, and suitably in an inert solvent, for example a basic solvent, such as pyridine, an ether, such as dioxane, or water.

Process (b) may also be carried out in conventional manner, for example by adding the compound of formula IV, in free base form, to a solution of the compound of formula III in an inert solvent, for example a chlorinated hydrocarbon, such as chloroform. The reaction is suitably effected at an elevated temperature, in particular at the reflux temperature of the reaction mixture.

Process (c) may be effected employing conventional acylating agents, for introduction of the $R_2CO$-group with simultaneous splitting off of the t-butyloxycarbonyl group (with evolution of $CO_2$) in compounds Ib, for example with mono- or dibasic acids, or their acid halides or anhydrides. The reaction is suitably effected at a temperature of from 20° to 150° C.

The resulting compounds of formula I may be isolated and purified using conventional techniques. Where required, free base forms of the compounds may be converted into acid addition salt forms in conventional manner, and vice versa.

The preferred compounds of formula I have the following significances of $R_1$, $R_2$ and X:

$R_1$: hydrogen or lower alkyl, particularly hydrogen or methyl, more particularly hydrogen;
$R_2$: hydrogen, lower alkoxy, in particular t-butoxy, amino, or trifluoromethyl, particularly hydrogen or t-butoxy;
X: oxygen or imino, particularly oxygen.

The most preferred compounds are those having combinations of the above significances.

The compounds of formula II may be obtained by reacting a compound of formula III, stated above, with an acid addition salt form of a compound of formula IV,

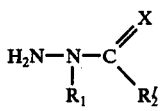   IV in which X, $R_1$ and $R_2'$ are as defined above.

The reaction is suitably effected in a polar solvent, for example a di-(lower) alkylamide, e.g. dimethylformamide and employing, for example, the hydrochloride form of the compound of formula IV.

The resulting compounds of formula II may be isolated and purified using conventional techniques. Where required free base forms of the compounds may be converted into acid addition salt forms in conventional manner, and vice versa.

Certain of the compounds of formula III, namely compounds of formula IIIa,

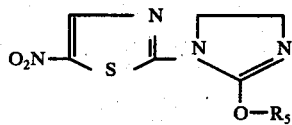   IIIa in which $R_5$ is as defined above,
are novel and may be produced by reacting a compound of formula VI,

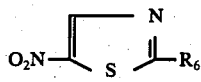   VI in which $R_6$ is halogen,
with a compound of formula VII,

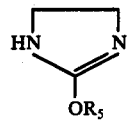   VII in which $R_5$ is as defined above. The reaction may, for example, be effected by dissolving or suspending the compound VI, in which $R_6$ suitably signifies bromine, in an inert solvent, for example dimethyl sulphoxide. The compound VII is then suitably added, preferably with cooling, and the mixture maintained at ambient temperature.

The resulting compounds of formula IIIa may be isolated and purified using conventional techniques.

The remaining compounds of formula III, i.e. those in which Z is sulphur, are known or may be produced in conventional manner from available materials.

The compounds of formula I are useful because they possess chemotherapeutic activity. In particular, they are useful in the treatment of helminthiasis, in particular trematodiasis, more particularly schistosomiasis, as indicated in in vivo tests in the mouse and hamster, in a dosage range of from 5 to 250 mg/kg of animal body weight administered daily on 5 consecutive days, orally and/or parenterally. The experimental methods employed correspond to those of J. Pellegrino and Naftale Katz, Advances in Parasitology 6 233–290 (1968) and Duvall, R. H. and De Witt, W. B., Am. J. Trop. Med. Hyg. 16, 483–486 (1967). Albino mice and hamsters, inoculated subcutaneously with 100 ± 10, or 60 ± 10 cercariae of Schistosoma mansoni (Liberiastrain) may be employed as test animals.

The compounds are also useful in the treatment of protozoal disorders, e.g. amoebiasis, trichomoniasisand coccidiosis. Their activity against amoeba and trichomonads is indicated in vitro by determination of the minimum lethal concentration in the series dilution test after 48 hours incubation at 37° C. The anti-trichomonad activity is determined by addition of the test substance to a T. Vaginalis culture in a CACH medium [Muller et.al., Angew. Parasit. 11, 170 (1970)] at concentrations of about 0.006 to 1.4 μ/ml. The amoebicidal activity is determined in a TTY-SB medium against monoxenically cultivated E. histolytica amoeba [Diamond, L. S., J. Parasit. 54, 715 (1968)] at concentrations of about 1.6 to 100 μ/ml. The anti-trichomonad activity is confirmed in vivo in the mouse. The amoebicidal activity is also indicated in vivo in the rat and hamster at a dosage of 50 to 150 mg/kg of animal body weight administered thrice.

The anti-coccidal activity is indicated in vivo in chicks. For example, when added to feed at concentrations of, for example, about 125 ppm, the compounds inhibit the course of infection of blind gut coccidiosis in chicks.

For the above-mentioned uses, the dosage administered will, of course, vary depending on the compound employed, mode of administration and treatment desired. However, for the treatment of schistosomiasis, amoebiasis and trichomoniasis, in general, satisfactory results are obtained when administered at a daily dosage of, respectively, from about 5 to 250 mg/kg, 5 to 150 mg/kg and 5 to 300 mg/kg of animal body weight, conveniently given in divided dosages two to four times daily, or in sustained release form. For the larger mammals, the corresponding total daily dosages are in the range, respectively, of 500 to 5000 mg, 400 to 3000 mg and 250 to 700 mg and dosage forms suitable for oral administration comprise from about 125 to 2500 mg, 100 to 1500 mg and 62.5 to 350 mg, respectively. For the treatment of coccidiosis in animals, the compounds are suitably added to animal food or drink as required, for example to food at a concentration of, for example, 125 ppm.

The preferred compounds for these uses include 1-(5-nitrothiazolyl-2)-2-(N-formylamino)iminoimidazolidine and 1-(5-nitrothiazolyl-2-[(N-trifluoroacetyl-N-methyl-)amino]iminoimidazolidine.

The compounds of formula I also possess inhibiting activity against bacteria, and are therefore useful as bacterial growth inhibitors, as indicated in vitro in the series dilution test at concentrations of from about 3 to 50 μ/ml and in vivo in the mouse at dosages of from about 25 to about 200 mg/kg of animal body weight, administered orally or sub-cutaneously, against a variety of bacterial strains, for example *Staph. aureus, E. coli, Shigella flexneri, Klebsiella pneumoniae* and Salmonella.

For this usage, the dosage to be administered will, of course, vary depending on the compound employed, mode of administration and treatment desired. However, in general, satisfactory results are obtained when administered at a daily dosage of from about 25 to about 200 mg/kg of animal body weight, conveniently given in divided doses two to four times daily, or in sustained release form. For the larger mammals, the daily dosage is from about 2 to 5 g, and dosage forms suitable for oral administration comprise from about 500 mg to 2.5 g.

For this usage, the preferred compounds include 1-(5-nitrothiazolyl-2)-2-(N-formylamino)iminoimidazolidine.

The compounds may be admixed with conventional chemotherapeutically acceptable diluents or carriers, and administered in such forms as tablets, capsules or injectable solutions.

The compounds may be used in free base form or in the form of their chemotherapeutically acceptable acid addition salts, which salt forms have the same order of activity as the free base forms.

The following Examples, in which all temperatures are in ° C, illustrate the invention.

EXAMPLE 1

1-(5-Nitrothiazolyl-2)-2-(N-ureido)iminoimidazolidine [process a)]

a)

1-{[(5-Nitrothiazolyl-2)amino]ethyl}-2-methyl-3-ureidoisothiourea

A mixture of 10 g of 2-methylmercapto-1-(5-nitrothiazolyl-2)-Δ$_2$-imidazoline and 5.3 g of semicarbazide hydrochloride in 100 ml of dimethylformamide is stirred at room temperature for 20 hours. The dimethylformamide is distilled off in vacuo at the lowest possible temperature and chloroform is added to crystallise the heading compound, in hydrochloride form, m.p. 230° (decomp.). Upon addition of an equimolar amount of sodium bicarbonate, to an aqueous solution of the hydrochloride form, the free base form, m.p. 230° –232°, may be obtained.

b)

1-(5-Nitrothiazolyl-2)-2-(N-ureido)iminoimidazolidine 4.1 g of 1-☐[(5-nitrothiazolyl-2)amino]ethyl}-2-methyl-3-ureidoisothiourea are suspended in 850 ml of water and the mixture is heated at reflux for 30 minutes, whereupon the compound is filtered off and washed with alcohol and ether. M.P. >300° (decomp.).

EXAMPLE 2

1-(5-Nitrothiazolyl-2)-2-(N-guanidino)iminoimidazolidine [process a)]

a)

1-{[(5-Nitrothiazolyl-2)amino]ethyl}-2-methyl-3-guanidinoisothiourea.

To a solution of 8.4 g of 2-methylmercapto-1-(5-nitrothiazolyl-2)-Δ$_2$-imidazoline in 80 ml of dimethyl formamide, is added 6 g of aminoguanidine hydrochloride. The mixture is stirred at room temperature for 20 hours and the precipitated heading compound, in dihydrochloride form, is filtered off and washed with chloroform, ethanol and ether, m.p. >195° (decomp.).

b)

1-(5-Nitrothiazolyl-2)-2-(N-guanidino)iminoimidazolidine

To a solution of 4.6 g of 1-{[(5-nitrothiazolyl-2) amino]ethyl}-2-methyl-3-guanidinoisothiourea, dihydrochloride form, in 190 ml of water, is added, carefully, 5.7 ml of 2N NaOH. The resulting precipitate is filtered off. The residue is refluxed in 80 ml of water for 15 minutes and cooled. The precipitate is filtered off and washed with isopropanol and ether to obtain the heading compound, in hydrochloride form, m.p. 215° –218° C (decomp.).

EXAMPLES 3 to 7

In manner analogous to that of Example 1 or 2, employing appropriate starting materials in approximately equivalent amounts, the following compounds may be obtained:

3a) 1-{[(5-nitrothiazolyl-2)amino]ethyl -2-methyl-3-[(N-t-butyloxycarbonyl)amino]isothiourea, m.p. 268° –271° b) 1-(5-nitrothiazolyl-2)-2-[N-t-butoxycarbonyl)amino]-iminoimidazolidine, m.p. 240° –242° (decomp.), 4a) 1-{[(5-nitrothiazolyl-2)amino]ethyl}-2-methyl-3-[(N-trifluoroacetyl)amino]isothiourea, b) 1-(5-nitrothiazolyl-2)-2-[(N-trifluoroacetyl)amino[-iminoimidazolidine, m.p. 252° –255° (decomp.), 5a) 1-{[(5-nitrothiazolyl-2)amino]ethyl}-2-methyl-3-[N-trifluoroacetyl-N-methyl)amino]isothiourea, b) 1-(5-nitrothiazolyl-2)-2-[N-trifluoroacetyl-N-methyl-)amino]iminoimidazolidine, m.p. >220° (decomp.), 6a) 1-{[(5-nitrothiazolyl-2)amino]ethyl}-2-methyl-3-[(N-formyl)amino]isothiourea, b) 1-(5-nitrothiazolyl-2)-2-[N-formyl)amino]-iminoimidazolidine,, m.p. 230° –240° C (decomp.), 7a) 1-{[(5-nitrothiazolyl-2)amino]ethyl}-2-methyl-3-(N-thioureido)isothiourea, m.p. 176° –178°, b) 1-(5-nitrothiazolyl-2)-2-(N-thioureido)iminoimidazolidine, m.p. 214° –217° C.

EXAMPLE 8

1-(5-Nitrothiazolyl-2)-2-[N-tert.butoxycarbonyl-)amino]iminoimidazolidine [Process b)]

38.2 g of 2-methylmercapto-1-(5-nitrothiazolyl-2)-$\Delta_2$-imidazoline is dissolved, at boiling temperature, in 800 ml of chloroform and 47.5 g of t-butylcarbazate is added to the resulting solution. The mixture is refluxed for 22 hours and then cooled. The precipitated heading compound is filtered off and washed with chloroform; m.p. 240° –242° C (decomp.).

EXAMPLE 9

1-(5-Nitrothiazolyl-2)-2-[(N-formyl)amino]-iminoimidazolidine [Process c)]

90 g of 1-(5-nitrothiazolyl-2)-2-[(N-t-butoxycarbonyl-)amino]iminoimidazolidine is slowly taken up in 900 ml of formic acid and the mixture is maintained at 80° until $CO_2$ evolution ceases. The clear solution is treated with active charcoal and filtered, and the filtrate is evaporated to dryness in vacuo. The residue is stirred with 500 ml of methanol, filtered and washed with ether to yield the heading compound, m.p. 230° –240° (decomp.).

EXAMPLES 10 to 13

[Process c)]

In manner analogous to that of Example 9, employing appropriate starting materials in approximately equivalent amounts, the following compounds may be obtained:

10. 1-(5-nitrothiazolyl-2)-2-[N-trifluoroacetyl-N-methyl)amino]iminoimidazolidine, m.p.>220° (decomp.),
11. 1-(5-nitrothiazolyl-2)-2-[(N-trifluoroacetyl)amino]-iminoimidazolidine,, m.p. 252° –255° (decomp.),
12. 1-(5-nitrothiazolyl-2)-2-[(N-acetyl)amino]-iminoimidazolidine, m.p.>280° (decomp.), and
13. 1-(5-nitrothiazolyl-2)-2-[N-(3-carboxypropenoyl-)amino]iminoimidazolidine, m.p. 210° (decomp.).

EXAMPLES 14 to 20

[Process (a) or (c)]

In manner analogous to the indicated Examples, and employing appropriate starting materials in approximately equivalent amounts, the compounds of formula I (and, where appropriate II) in which $R_1$, $R_2$ and X are as defined in the following Table, may be obtained:

| Example | Analogy to Example | $R_1$ | $R_2$ | X | Process |
|---|---|---|---|---|---|
| 14 | 1, 2 or 9 | $CH_3$ | H | NH | a), c) |
| 15 | 1, 2 or 9 | H | t-butoxy | NH | a), c) |
| 16 | 1, 2 or 9 | $CH_3$ | $CF_3$ | NH | a), c) |
| 17 | 1, 2 or 9 | $C_6H_5$ | H | O | a), c) |
| 18 | 1, 2 or 9 | $CH_3$ | $-N(CH_3)_2$ | O | a), c) |
| 19 | 1, 2 or 9 | $CH_3$ | t-butoxy | O | a), c) |
| 20 | 1, 2 or 9 | $CH_3$ | H | O | a), c) |

What is claimed is:
1. Compounds of formula I,

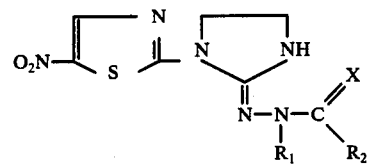

in which $R_1$ is hydrogen, lower alkyl or phenyl,
  $R_2$ is hydrogen, lower alkyl or alkoxy, trifluoromethyl, the group —CH=CH—COOH or a group —N($R_3$)($R_4$), in which $R_3$ and $P_4$, which may be the same or different, each signifies hydrogen or lower alkyl, and
  X is oxygen, sulphur or imino, provided that when $R_2$ is lower alkyl or —CH=CH—COOH, then X is oxygen,
or a chemotherapeutically acceptable acid addition salt thereof.
2. Compounds of claim 1, in which X is oxygen.
3. Compounds of claim 1, in which X is imino.
4. The compound of claim 1, which is 1-(5-nitrothiazolyl-2)-2-(N-formylamino)iminoimidazolidine.
5. The compound of claim 1, which is 1-(5-nitrothiazolyl-2)-2-[(N-trifluoroacetyl-N-methyl)amino]-iminoimidazolidine.
6. The compound of claim 1 which is 1(5-nitrothiazolyl-2)-2-(N-ureido) iminoimidazolidine.
7. The compound of claim 1 which is 1-(5-nitrothiazolyl-2)-2-(N-guanidino) iminoimidazolidine.
8. The compound of claim 1 which is 1-(5-nitrothiazolyl-2)-2- [(N-t-butoxycarbonyl) amino]-iminoimidazolidine.
9. The compound of claim 1 which is 1-(5-nitrothiazolyl-2)-2- [(N-trifluoroacetyl)amino]-iminoimidazolidine.
10. The compound of claim 1 which is 1-(5-nitrothiazolyl-2)-2-(N-thioureido) iminoimadazolidine.
11. The compound of claim 1 which is 1-(5-nitrothiazolyl-2)-2- [(N-acetyl) ammino]iminoimidazolidine.
12. The compound of claim 1 which is 1-(5-nitrothiazolyl-2)-2-[N-(3-carboxypropenoyl) amino]-iminoimidazolidine.

* * * * *